US009968279B2

(12) United States Patent
Dumoulin

(10) Patent No.: US 9,968,279 B2
(45) Date of Patent: May 15, 2018

(54) MRI TRANSFER TABLE ASSEMBLY

(75) Inventor: Charles L. Dumoulin, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 946 days.

(21) Appl. No.: 14/376,523

(22) PCT Filed: Aug. 24, 2012

(86) PCT No.: PCT/US2012/052249
§ 371 (c)(1),
(2), (4) Date: Aug. 15, 2014

(87) PCT Pub. No.: WO2013/115847
PCT Pub. Date: Aug. 8, 2013

(65) Prior Publication Data
US 2014/0364722 A1 Dec. 11, 2014

Related U.S. Application Data

(60) Provisional application No. 61/593,930, filed on Feb. 2, 2012.

(51) Int. Cl.
A61B 5/00 (2006.01)
A61B 5/055 (2006.01)
A61G 11/00 (2006.01)
G01G 19/44 (2006.01)

(52) U.S. Cl.
CPC .......... A61B 5/0555 (2013.01); A61B 5/0046 (2013.01); A61G 11/005 (2013.01); G01G 19/44 (2013.01); A61B 2503/045 (2013.01)

(58) Field of Classification Search
CPC ................ A61B 5/0555; A61B 5/0046; A61B 2503/045; A61G 11/005; G01G 19/44
See application file for complete search history.

(56) References Cited

U.S. PATENT DOCUMENTS

| 4,665,364 A | 5/1987 | Hanawa |
| 4,727,328 A | 2/1988 | Carper et al. |
| 5,178,146 A | 1/1993 | Giese |
| 5,515,415 A | 5/1996 | Herrmann et al. |

(Continued)

FOREIGN PATENT DOCUMENTS

| WO | 1996/029932 A1 | 10/1996 |
| WO | 2013/001847 A1 | 10/1996 |

(Continued)

OTHER PUBLICATIONS

Extended European Search report from EP application 12867342, dated Jul. 1, 2015, 7 pages, mailed from European Patent Office, Munich, Germany.

(Continued)

Primary Examiner — Joel Lamprecht
(74) Attorney, Agent, or Firm — Baker & Hostetler LLP

(57) ABSTRACT

The present disclosure relates to a transfer table assembly suitable for use in association with an MR scanner. The transfer table assembly includes a transfer table attached to a transfer table base that may releasably engage an incubator. The transfer table may be dimensionally constructed such that it may be inserted directly into an MR scanner.

27 Claims, 8 Drawing Sheets

(56) References Cited

U.S. PATENT DOCUMENTS

| | | | |
|---|---|---|---|
| 5,619,763 | A | 4/1997 | Randolph et al. |
| 5,650,724 | A | 7/1997 | Yamagata |
| 5,724,970 | A | 3/1998 | Votruba et al. |
| 5,792,041 | A | 8/1998 | Kobayashi et al. |
| 5,800,335 | A | 9/1998 | Koch et al. |
| 6,101,644 | A | 3/2000 | Gagneur |
| 6,377,047 | B1 | 4/2002 | Wong |
| 6,611,702 | B2 | 8/2003 | Rohling et al. |
| 6,718,571 | B2 | 4/2004 | Bartels |
| 6,854,140 | B2 | 2/2005 | Bartels et al. |
| 7,093,311 | B2 | 8/2006 | Gnoyke |
| 7,131,769 | B2 | 11/2006 | Vezina |
| 7,216,383 | B2 | 5/2007 | Heini et al. |
| 7,467,004 | B2 | 12/2008 | Calderon et al. |
| 7,599,728 | B2 | 10/2009 | Feenan |
| 7,634,827 | B2 | 12/2009 | Gagneur et al. |
| 7,827,635 | B2 | 11/2010 | Wang et al. |
| 7,850,595 | B2 | 12/2010 | White |
| 7,869,858 | B2 | 1/2011 | Calderon et al. |
| 7,874,030 | B2 | 1/2011 | Cho et al. |
| 7,920,910 | B2 | 4/2011 | Calderon et al. |
| 8,147,396 | B2 | 4/2012 | Srinivasan |
| 8,276,225 | B2 | 10/2012 | Kogan et al. |
| 2001/0052168 | A1 | 12/2001 | Haase et al. |
| 2002/0104163 | A1 | 8/2002 | Reimann |
| 2002/0158720 | A1 | 10/2002 | Weyers et al. |
| 2002/0173717 | A1 | 11/2002 | Rohling et al. |
| 2003/0153805 | A1 | 8/2003 | Gryn et al. |
| 2005/0034237 | A1 | 2/2005 | Lenting et al. |
| 2005/0113668 | A1* | 5/2005 | Srinivasan ............ A61B 5/416 600/411 |
| 2006/0293589 | A1 | 12/2006 | Calderon et al. |
| 2007/0132581 | A1 | 6/2007 | Molyneaux et al. |
| 2007/0232894 | A1 | 10/2007 | Feenan |
| 2008/0117044 | A1 | 5/2008 | Hibbs |
| 2008/0201849 | A1 | 8/2008 | Van Es et al. |
| 2009/0000917 | A1 | 1/2009 | Tigwell et al. |
| 2009/0027053 | A1 | 1/2009 | Decke et al. |
| 2009/0083907 | A1 | 4/2009 | Ahlman |
| 2010/0185045 | A1 | 7/2010 | Chinn |
| 2011/0113555 | A1 | 5/2011 | Smith |
| 2011/0145991 | A1 | 6/2011 | Bridge et al. |
| 2012/0071745 | A1 | 3/2012 | Rapoport |
| 2013/0025054 | A1 | 1/2013 | Graw et al. |
| 2013/0109956 | A1 | 5/2013 | Rapoport |
| 2013/0150656 | A1 | 6/2013 | Falk et al. |

FOREIGN PATENT DOCUMENTS

| | | |
|---|---|---|
| WO | 2013115846 A1 | 8/2013 |
| WO | 2013115848 A1 | 8/2013 |

OTHER PUBLICATIONS

Dumoulin, Charles L., et al., Magnetic Resonance Imaging Compatible Neonate Incubator, Magnetic Resonance Engineering, Jun. 28, 2002, vol. 15 (2), pp. 117-128.

European Patent Application No. 12867132.8; Extended Search Report; dated Sep. 16, 2015; 6 pages.

European Patent Application No. 12867263.1; Extended Search Report; dated Sep. 16, 2015; 7 pages.

Dumoulin, Charles L., et al., Magnetic Resonance Imaging Compatible Neonate Incubator, Magnetic Resonance Engineering, Jun. 28, 2002, vol. 15 (2), pp. 117-128, US.

PCT International Search Report/Written Opinion, PCT/US2012/052242, dated Nov. 2, 2012.

PCT International Search Report/Written Opinion, PCT/US2012/052249, dated Nov. 2, 2012.

PCT International Search Report/Written Opinion, PCT/US2012/052260 dated Nov. 2, 2012.

* cited by examiner

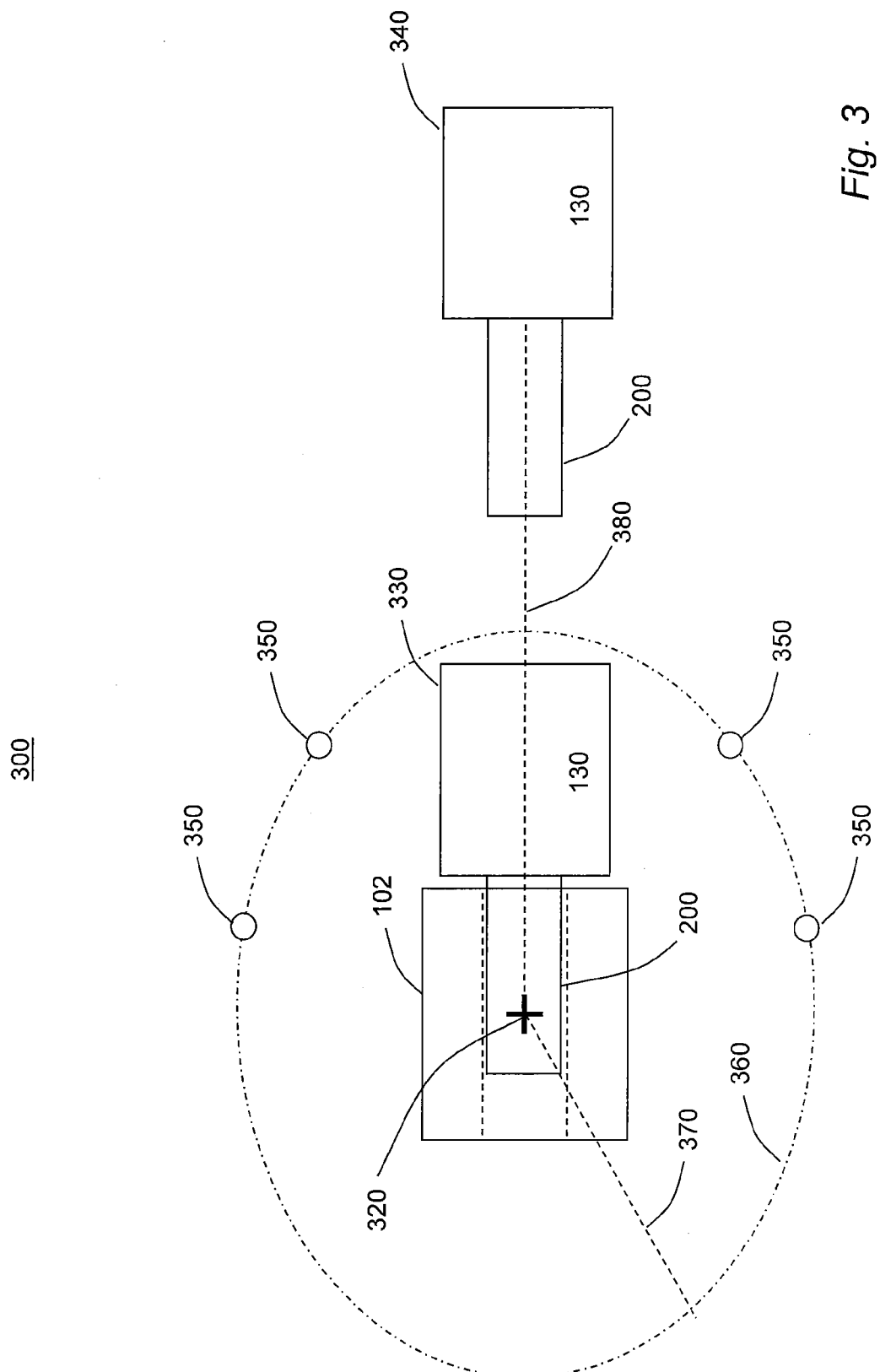

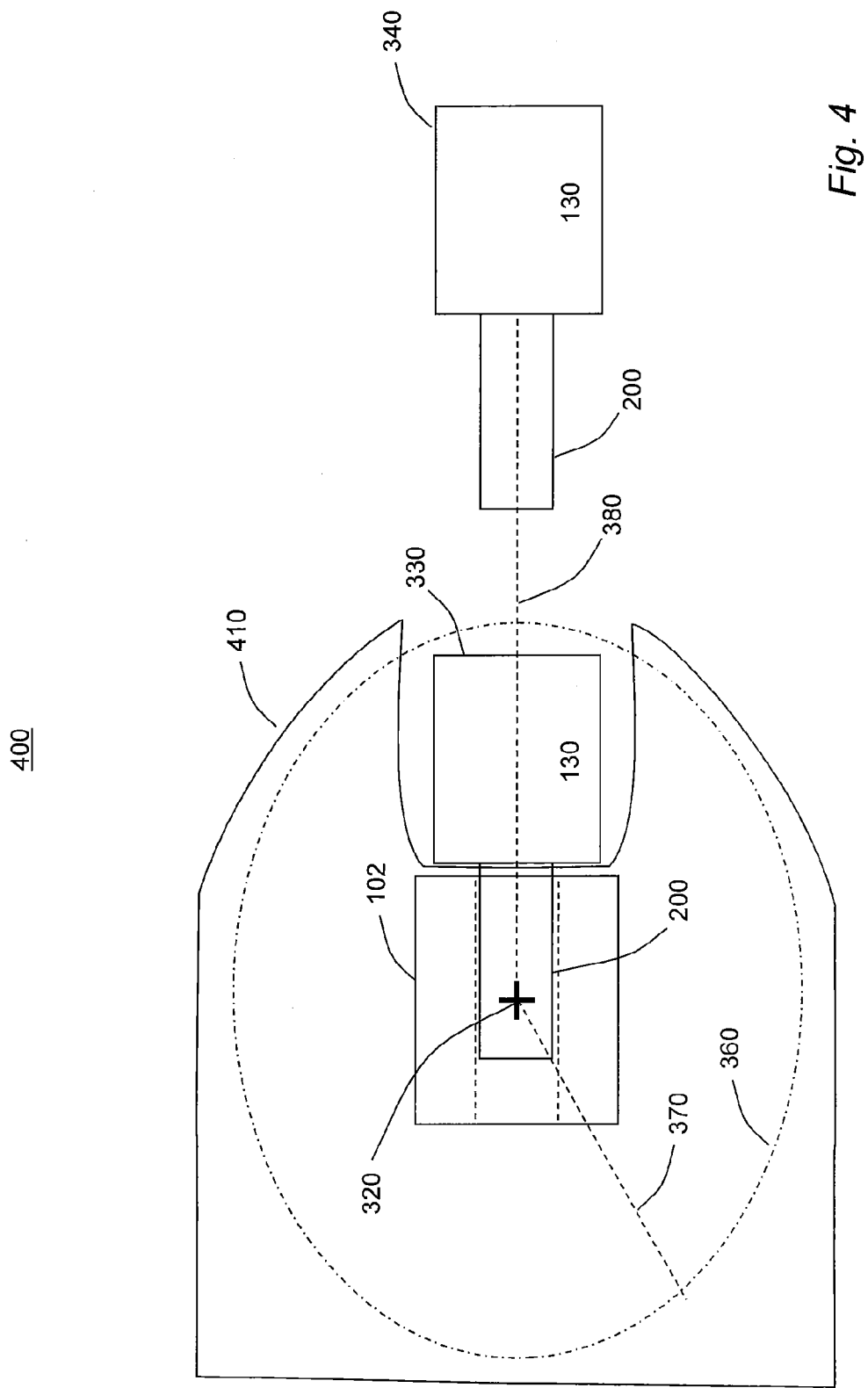

MRI TRANSFER TABLE ASSEMBLY

CROSS-REFERENCE TO RELATED APPLICATIONS

The present application is a national stage entry of PCT/US2012/052249, filed Aug. 24, 2012, which claims priority benefit of U.S. Provisional Patent Application Ser. No. 61/593,930 filed Feb. 2, 2012 and is further related to U.S. Provisional Patent Application Ser. No. 61/429,612 also filed Jan. 4, 2011.

FIELD OF THE DISCLOSURE

The present disclosure relates generally to magnetic resonance imaging equipment suitable for use in neonatal care and, more particularly, to a transfer table assembly for transferring a neonate from an incubator into an MR scanner.

BACKGROUND OF THE DISCLOSURE

Today premature infants weighing less than 1 kg may be stabilized and allowed to develop in neonatal intensive care units (NICUs). Magnetic resonance imaging (MRI) is a powerful technique for diagnostic purposes but is not routinely performed on these infants due to a number of technical and logistical challenges.

When a mother has a high-risk pregnancy, it is possible that the baby could be born prematurely and would require treatment in a neonatal intensive care unit or NICU. Also, unexpected early delivery may require that an infant be treated in an NICU.

One difficulty in utilizing MRI for these premature infants is monitoring the vital signs and life support of the infant during MR examination. Parameters that must be monitored during examination include electrolyte levels, hydration and temperature. A second difficulty in utilizing MRI is that the infant must be moved from an incubator or isolette into and out of the MR scanner. This movement places the infant at risk for injury.

Despite challenges, MRI has the potential to play an important diagnostic role in the care and management of neonates. The full use of this imaging technique requires that the imaging take place as early as the first few hours of life. At this stage, however, the infants are hemodynamically unstable. Accordingly, transporting and maintaining homeostasis in these fragile infants presents difficulty.

Another challenge in using MRI for neonates is that MRI systems are frequently located in Radiology departments outside of and perhaps distant from the NICU. Consequently, the neonate must be escorted out of the NICU. This may present certain logistical and technical challenges with respect to controlling the neonate's environment. Furthermore, removing staff from the NICU to transfer and attend to one baby outside the NICU can place the remaining babies in the NICU at increased risk of a reduced level of care due to decreased staff coverage.

An MR compatible transport incubator and imaging system has been developed (Dumoulin et. al.) and is currently in use. Concepts in Magnetic Resonance (Magnetic Resonance Engineering), Vol. 15(2) 117-128 (2002). This system is a self-contained MR compatible transport incubator which carries the infant from the NICU to an MR scanner located in or near the NICU. With this approach the baby must first be transferred from its "home" incubator or isolette in the NICU into the transport incubator. The transport incubator is then moved to the MR scanner where it is docked with the scanner. A portion of the transport incubator containing the baby is then moved into the center of the MR imaging system magnet where MR imaging is performed. While this approach has the advantage of not disturbing the baby while it is in the transport incubator, even during MR scanning, it has several limitations including: a) infants must be fully detached from the monitoring equipment in their home incubator to be transferred into the transport incubator, b) the MR system that is used for imaging must have a bore large enough to accommodate the portion of the transport incubator containing the baby (thereby requiring a large heavy magnet), c) the baby and its attending staff need to leave the NICU for scanning, and d) because the transport incubator must be fully MR compatible while providing full life support for the baby, the system is heavy and expensive.

An alternate approach to provide MR imaging to newborn babies has been disclosed by Feenan in U.S. Pat. No. 7,599,728. In this approach a relatively smaller MR magnet is employed and MR-compatible incubators are docked to the magnet thereby permitting the baby to be slid into the magnet for imaging. While this approach has the benefit of providing a magnet that is more easily installed in the NICU, it does have several limitations including the need for MR compatible incubators to be used throughout the NICU, or the transfer of a neonate from a non-MR-compatible home incubator to an MR-compatible incubator. This approach also limits the access to the attending staff as they prepare the infant for MR scanning. In particular, the staff must reach through the incubator to push the baby into and out of the magnet.

In view of the foregoing, it may be understood that improved techniques for neonatal care necessitate improved transfer techniques for neonates in NICUs. In particular there is a need for an MR neonatal imaging system that can be easily sited in the NICU. The NICU magnet should be small, lightweight and acoustically quiet to permit installation within the physical boundaries of the NICU. Furthermore, there is a need for MR imaging of neonates without requiring them to be transferred out of their home incubators, or detaching them from their physiological monitoring systems or intravenous tubes. There is also a need to minimize physical movement of the baby as it enters the MR magnet and to ensure that it stays still during MR scanning. There is an additional need to for a neonatal MR imaging system that will allow babies in the NICU to be imaged without requiring that incubators in the NICU be MR compatible.

SUMMARY

A transfer table assembly is disclosed that is suitable for use in association with an MR scanner and an incubator for neonatal infants. The transfer table assembly generally includes a transfer table base that supports a transfer table. The transfer table may be removably connected with the top surface of the transfer table base. An associated incubator may include a bed for supporting a neonate when being cared for in the incubator. The transfer table may be configured to receive the incubator bed and the patient. In order to provide additional support and stability, the transfer table assembly may include an attachment mechanism for releasably attaching the transfer table base to the incubator in such a manner that said transfer table is substantially at the same level of the incubator bed. Additionally, the transport table assembly may include a supporting mechanism for providing additional structural support to the transfer table base when the transfer table base is attached to the incubator.

The present disclosure will now be described in more detail with reference to exemplary embodiments thereof as shown in the accompanying drawings. While the present disclosure is described below with reference to exemplary embodiments, it should be understood that the present disclosure is not limited thereto. Those of ordinary skill in the art having access to the teachings herein will recognize additional implementations, modifications, and embodiments, as well as other fields of use, which are within the scope of the present disclosure as described herein, and with respect to which the present disclosure may be of significant utility.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be exemplary only.

FIG. 3 shows a top-plan view of an MR magnet and incubator with barrier poles to limit access of the incubator to the magnet; and FIG. 4 shows a top-plan view of an MR magnet and incubator with an elevated floor barrier to limit access of the incubator to the magnet.

DETAILED DESCRIPTION

Figure 1A:
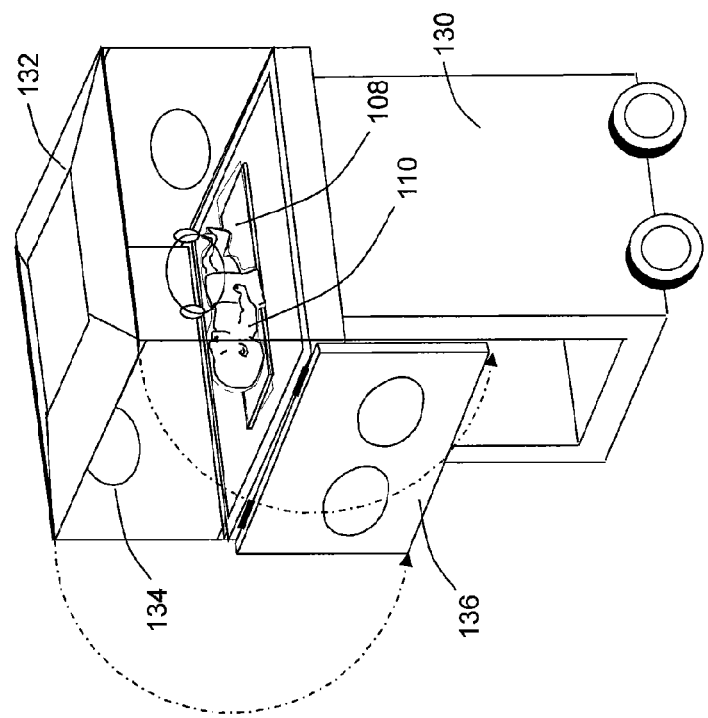
FIG. 1a is a perspective view of an exemplary MR imaging system and an exemplary incubator containing a neonate for use with the present disclosure.
Figure 1A:
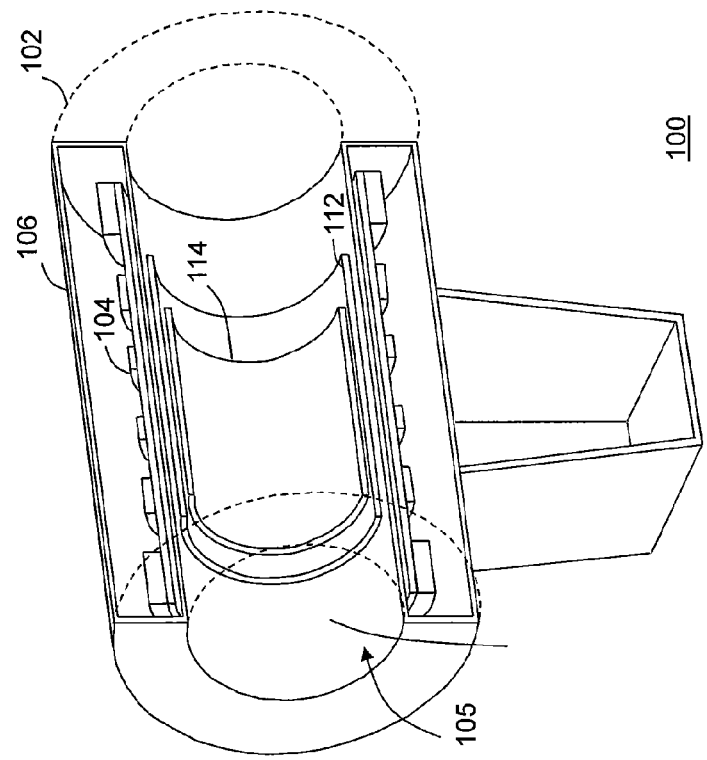

The use of MRI techniques for infants, and in particular neonates, is highly desirable. MRI techniques provide diagnostic information without patient exposure to ionizing radiation, and are suitable for extended and repeated studies.

MR techniques provide excellent anatomic visualization and functional information. They can be used to measure neural fiber track development and have a number of potential clinical uses including, but not limited, to diagnosis of brain trauma, cardiac abnormalities, congenital defects and the assessment of lung development.

There are, however, a number of challenges in the use of MRI for neonatal imaging. Patient access during scanning can be difficult as MR magnets are typically large and surround the patient. Safety concerns include forces on ferromagnetic objects, potential for rf heating and acoustic noise. Also, logistics may be difficult, as MR scanners tend to be in radiology departments, while neonate infants are typically in the NICU.

FIGS. 1a-1d depict an exemplary MRI and incubator system 100 in or for which the techniques for the MR imaging of neonates in accordance with the present disclosure may be implemented. The illustrated MRI system comprises an MRI scanner 102. Since the components and operation of the MRI scanner are well-known in the art, only some basic components helpful in the understanding of the system 100 and its operation will be described herein.

The MRI scanner 102 may comprise a cylindrical superconducting magnet 104, which generates a static magnetic field within a bore 105 of the superconducting magnet 104. The superconducting magnet 104 generates a substantially homogeneous magnetic field within the magnet bore 105. The superconducting magnet 104 may be enclosed in a magnet housing 106.

A set of cylindrical magnetic field gradient coils 112 may also be provided within the magnet bore 105. The gradient coils 112 can generate magnetic field gradients of predetermined magnitudes, at predetermined times, and in three mutually orthogonal directions within the magnet bore 105. With the field gradients, different spatial locations can be associated with different precession frequencies, thereby giving an MR image its spatial resolution. An RF transmitter coil 114 is positioned within the gradient coils 112. The RF transmitter coil 114 emits RF energy in the form of a magnetic field for the purpose of exciting MR signals during image acquisition. The RF transmitter coil 114 can also receive MR response signals. The MR response signals are amplified, conditioned and digitized into raw data as is known by those of ordinary skill in the art.

The present disclosure provides an apparatus and a technique for safely and effectively transferring an infant from the primary care area, such as an incubator, to the MR magnet. In one particular embodiment, the present disclosure provides the means to transfer a neonate from the NICU to an MR magnet located either in a radiology department or in the NICU itself. The present disclosure accomplishes this by providing an MR-compatible transfer table assembly that can be easily attached to and removed from the infant's incubator without disturbing the infant. This assembly creates an MR compatible extension to the incubator that the baby can be moved into without being detached from patient monitoring or life support systems. Once stabilized in the assembly, the incubator, baby and transfer table assembly can then be moved as a unit to the magnet, where the transfer table assembly and baby are inserted into the magnet, without the need to insert the incubator into the magnet. In the present disclosure the incubator does not need to be fully MR compatible and can be constructed with some MR incompatible elements such as electrical motors.

Referring again to FIGS. 1a-1d, an incubator 130 containing a neonate 110 lying on an incubator bed 108 is shown. The incubator 130 has an optional top 132 that can be left in place or alternatively moved away from the neonate. The walls of the incubator may be clear and may provide one or more incubator access ports 134 to permit attending medical staff to reach into the incubator. The incubator may have a front panel 136 that can be removed or rotated out of the way to provide wider access to the neonate 110.

Figure 1B:
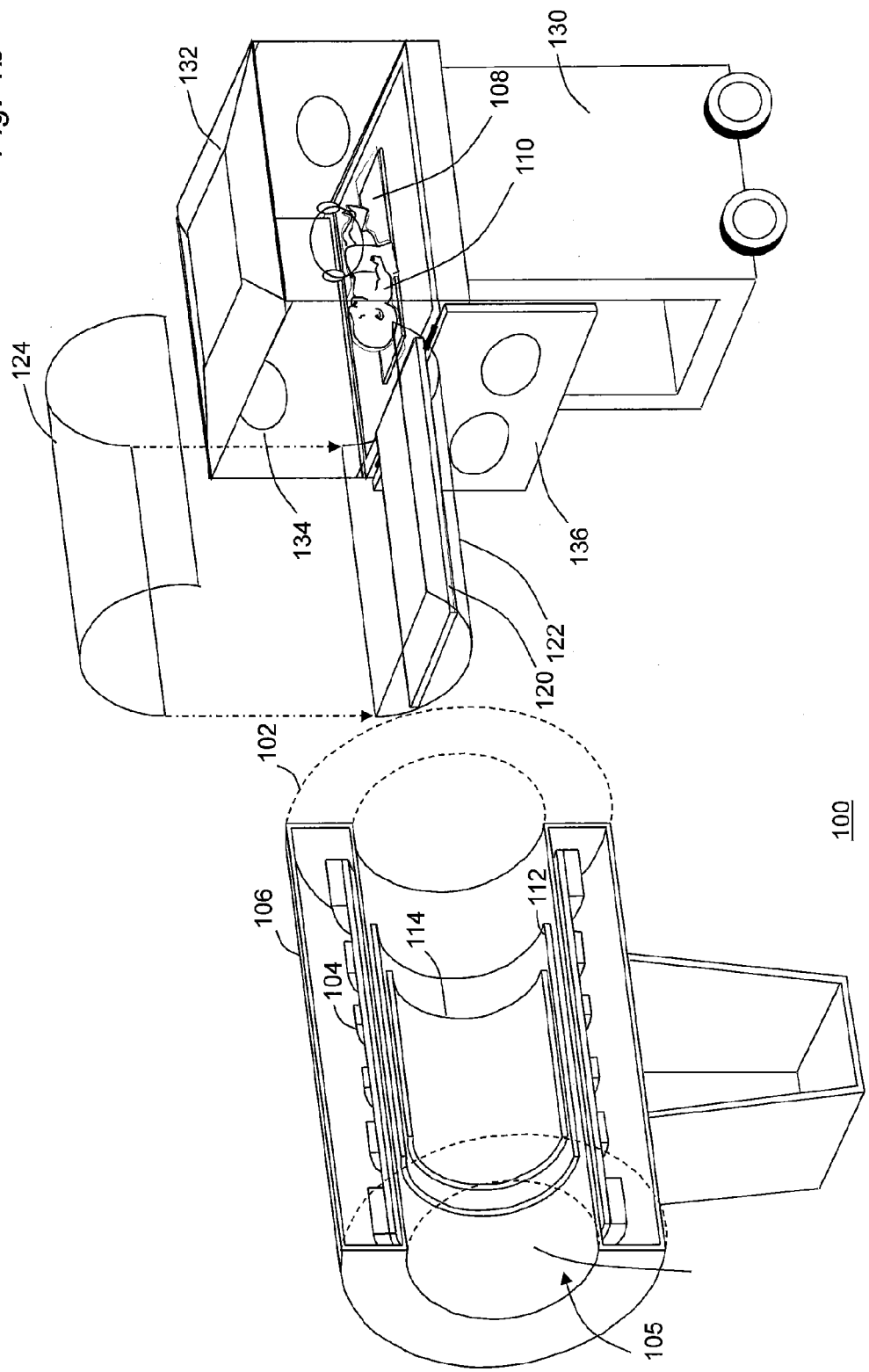
FIG. 1b is a perspective view further showing the attachment of the transfer table assembly to an incubator in accordance with the present disclosure.

FIG. 1b shows the attachment of a transfer table assembly according to the present disclosure (shown later as element 200 of FIG. 2) to the incubator 130. This transfer table assembly according to the present disclosure may include of a transfer table 120, a transfer table base 122 and a transfer table cover 124. The transfer table 120 may be positioned at substantially the same level as the base of the incubator bed 108 and is designed to receive and support all or a portion of the incubator bed 108. The transfer table base 122 may serve to support the transfer table 120, and in one embodiment may be constructed with clear plastic. In one embodiment of the present disclosure, the transfer table cover 124 may also constructed of clear plastic. The transfer table cover may optionally be attached by hinges to the transfer table base 122 or, in another embodiment, may be inserted with locking pins or other affixation mechanisms. In another embodiment of the disclosure, the transfer table cover 124 can be made removable and not used if desired.

Figure 1C:
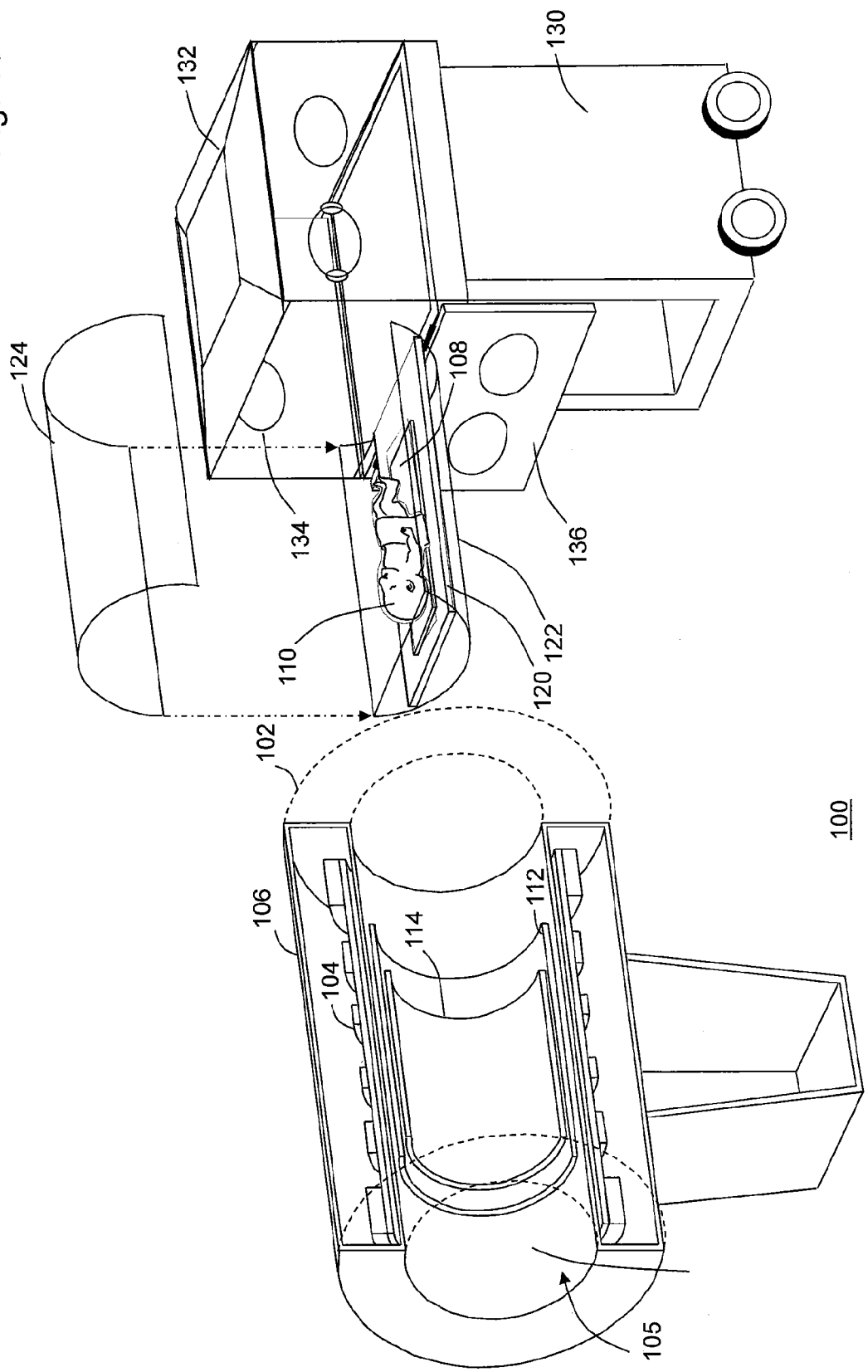
FIG. 1c is a perspective view showing the placement of a neonate into the transfer table assembly while attached to the incubator.

FIG. 1c shows the placement of the neonate 110 and incubator bed 108 on the transfer table 120. In one embodiment of the present disclosure, neonate 110 is prepared for MR scanning while in this location. Preparations may include but are not limited to patient safety checks, swaddling, attachment of additional monitoring equipment, placement of MR receive coils, and/or attachment of hearing protection to the neonate 110.

Figure 1D:
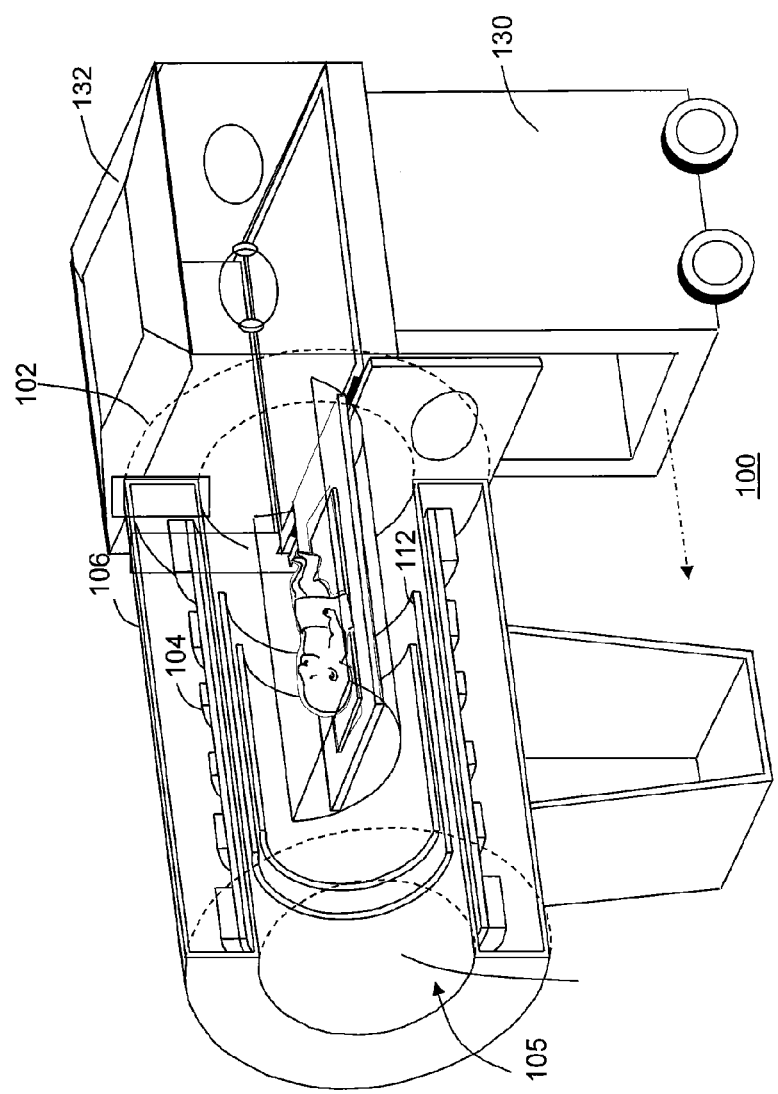
FIG. 1d is a perspective view showing the placement of the ensemble of incubator, transfer table assembly and neonate into an MR imaging system.

FIG. 1d shows the insertion of the transfer table assembly with the neonate into the MR imaging system 102. Note that during this insertion the neonate is not moved with respect to the incubator bed 108, the incubator 130, or the transfer table assembly.

Figure 2:
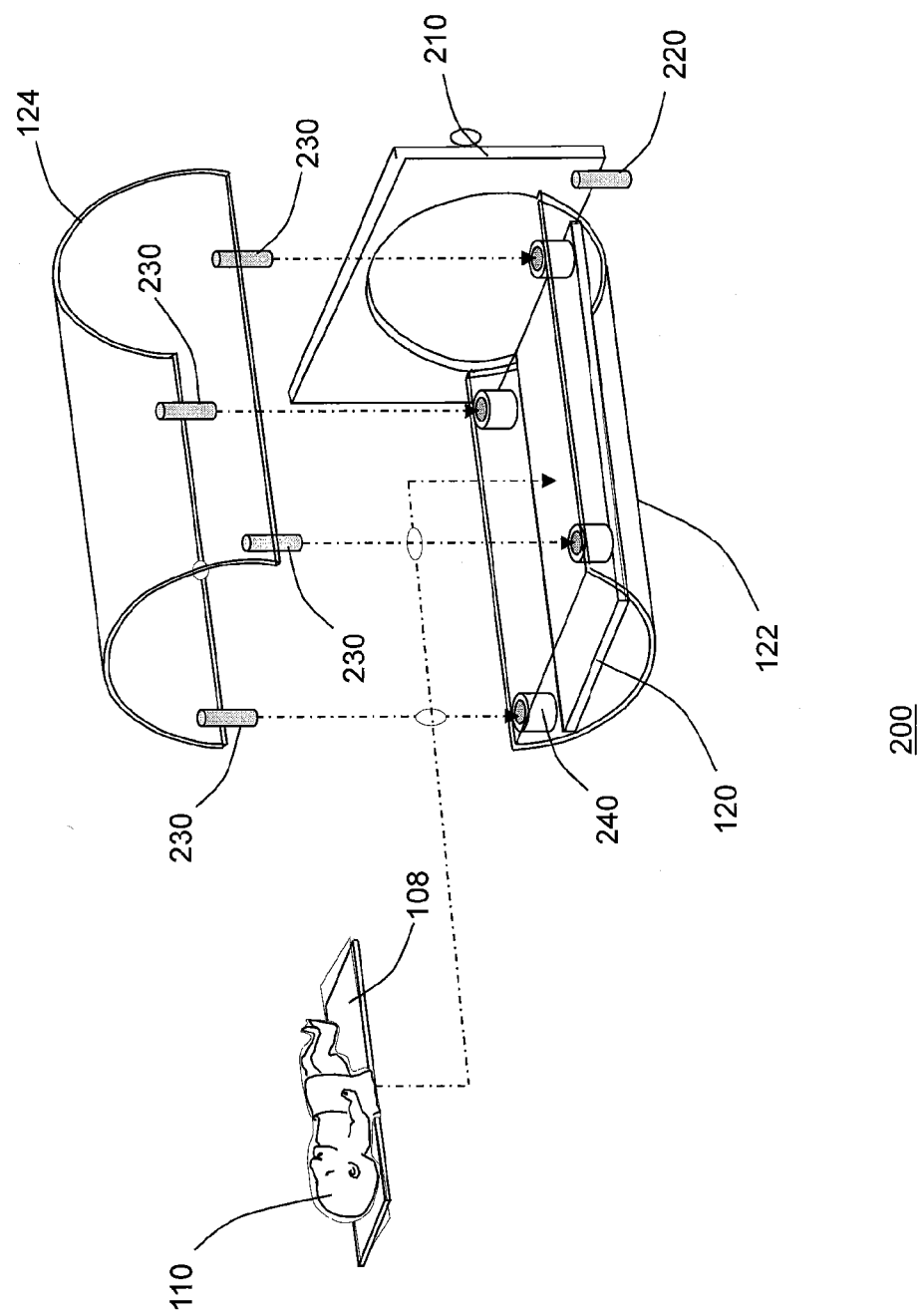
FIG. 2 is a partially exploded perspective view showing an embodiment of the MR-compatible transfer table assembly of the present disclosure.

FIG. 2 shows one embodiment of a transfer table assembly 200 in greater detail. The transfer table assembly 200 may include the transfer table 120, the transfer table base 122 and the transfer table cover 124. The transfer table base 122 and transfer table 120 may be attached to an end plate 210 which may provide additional structural support and serve to keep the incubator 130 enclosed when the incubator front panel 136 is not in position. End plate 210 may incorporate one or more assembly insertion pins 220 that are configured to align and attach the transfer table assembly 200 to the incubator 130. The pin assembly shown here is exemplary. It should be understood that the attachment of the transfer table assembly 200 to the incubator 130 can be accomplished by alternative means including, but not limited to, wing-nuts, slots, clamps and the like. Transfer table base 122, transfer table cover 124, and the end plate may be constructed of clear plastic material. The endplate may be formed from non-metallic material although small amounts of MR compatible metals such as aluminum, stainless steel, brass, etc. may be used. In one embodiment, the transfer table cover 124 may incorporate one or more cover locking pins 230 that may be designed for insertion into a like number of corresponding cover pin sockets 240. The cover locking mechanism shown here is exemplary. It should be understood that alternate mechanisms for attaching the transfer table cover 124 to the transfer table base 122, including, but not limited to hinges, slots, clamps and slides are covered by the spirit of the disclosure. If desired, neonate access ports similar to the incubator access ports 134 found in the incubator 130 can be incorporated into the transfer table cover 124. It should be obvious to one skilled in the art that the transfer table assembly may be constructed using MR compatible materials. It should also be obvious to one skilled in the art that the walls of the transfer table cover may be designed to attenuate the acoustic noise for the neonate 110.

Figure 2A:
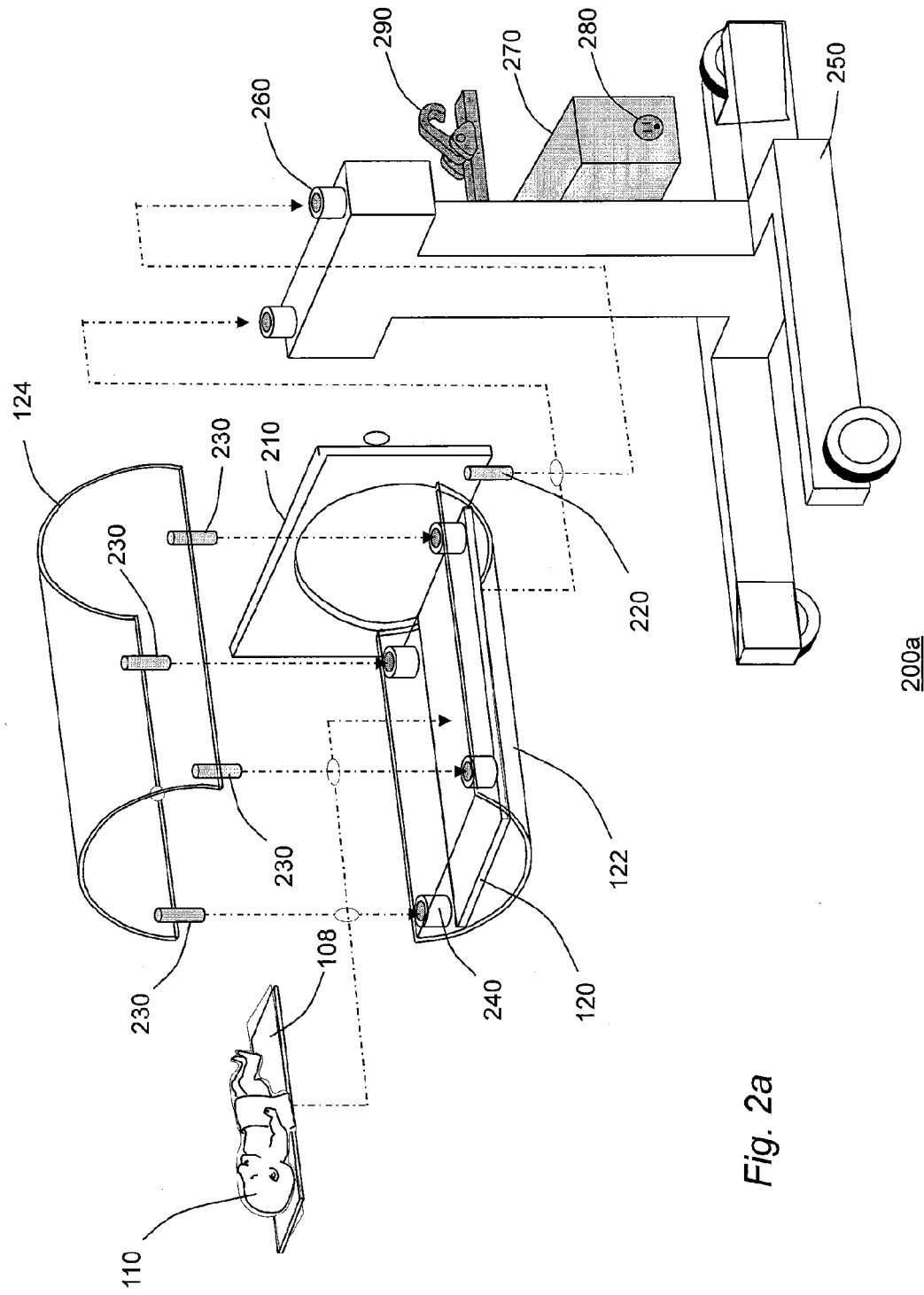
FIG. 2a is a partially exploded perspective view of an alternate embodiment of the MR-compatible transfer table assembly adapted to be secured to a cart.

FIG. 2a shows an alternate embodiment 200a of the transfer table assembly. In this embodiment, the assembly itself is substantially the same as disclosed in FIG. 2, but incorporates the ability to be attached to a transfer table cart 250. Transfer table cart 250 may have one or more sockets 260 for receiving the assembly insertion pins 220. It should be understood that the attachment of the transfer table assembly 200a to the transfer table cart 250 can be accomplished by alternative means including, but not limited to, wing-nuts, slots, clamps and the like. Transfer table cart 250 may incorporate several features including a frame and wheel design that permits the transfer table cart 250 to dock to the MRI scanner 102. This allows the transfer table assembly to be inserted into the magnet while the transfer table cart 250 is supporting the weight of the transfer table assembly. In yet another embodiment of the disclosure, transfer table cart 250 may incorporate a docking mechanism 290 for attaching the transfer table cart 250 to the incubator 130. This provides for a way to affix the transfer table assembly 200 to the incubator 130 without requiring lifting of the transfer table assembly 200 and without requiring the incubator 130 to support a substantial portion of the weight of the transfer table assembly 200. In another embodiment of the transfer table cart 250, a power supply 270 is incorporated into the cart. The power supply 270 may incorporate a battery pack and inverter to provide AC power to the incubator 130 via an on-board electrical socket 280.

The present disclosure is particularly advantageous in that it may minimize the transfer time from the NICU to an MR imaging system 102 and may provide less stress on the infant. Another advantage of the present disclosure is that babies do not need to be fully detached from their home incubator which is shown as incubator 130 in FIGS. 1a-1d. Physiological monitoring leads, IV tubes, ventilator tubes and temperature sensors can be left in place throughout the imaging process. This further reduces preparation times and stress on the infant. An important aspect of the present disclosure is that the infant can be prepared for MR scanning while the incubator 130 and transfer table assembly are outside of the magnet. Once the baby is stabilized, the ensemble of baby, transfer table assembly and incubator can be inserted into the magnet to place the baby in the imaging region of the MRI scanner. This approach ensures that the local environment of the baby is not altered as it is brought into the center of the imaging system. Furthermore, because a transport incubator is not required, and since the home incubator need not be fully MR-compatible, the MR magnet can be small and lightweight. This makes it more easily installed within the confines of the NICU, and provides improved access to MR for premature babies. In addition, the present disclosure permits MR scanning to be performed with fewer support personnel, and/or places support personnel closer to the other babies present in the NICU. With the present disclosure MR imaging may be made available to all babies in a NICU (typically between 10 and 60) using a single MR magnet and a single transfer table assembly that may be installed as needed into each and every compatible incubator in the NICU.

In particular, the present disclosure relates to a transfer table assembly for preparing an infant, including neonates, prior to transfer into the magnet. In the present disclosure the transfer table assembly is an extension that may be selectively physically attached to an incubator 130 that is actively supporting an infant. In a typical embodiment, one wall of the incubator may be removed or repositioned out of the way. The transfer table assembly may then attached to the incubator 130. The assembly may be designed to expand the interior volume of the incubator, but may have an external profile that permits the assembly to be inserted into an MR imaging system. The assembly may incorporate a platform that permits the neonate to be moved from its position in the incubator into the table assembly. The platform may be constructed to permit the infant's bed, or a portion of the bed, to be rolled from the incubator into the table assembly without disturbing or touching the infant.

Once the infant is in the MR-compatible transfer table assembly 200, the infant may be prepared for MR scanning. As will be recognized by those skilled in the art of MR scanning, MR scanning frequently requires that several steps be performed before a patient can be inserted into an imaging magnet. These steps may include: a) immobilization of the patient (in the case of neonatal imaging, swaddling is frequently sufficient), b) the optional insertion of IV tubes for contrast injections, c) the attachment of MR imaging coils, d) a safety check to verify that no ferromagnetic objects are present, e) placement of hearing protection, and f) verification of patient stability and comfort. All of these steps may need to be performed while the patient is near the magnet, and may require access to the patient which is not possible with most incubator designs.

Another aspect of the transfer table assembly of the present disclosure is that it may provide full environmental control for the neonate. Many neonates are too young to be able to fully control their internal temperature, and it is well known to those skilled in the art that small neonates must be kept warm. In the present disclosure, this can be done with warm air and/or a radiant heater located in the infants incubator 130. In one embodiment of the disclosure, a thermocouple or similar temperature sensor modified for use in the MR environment with non-ferromagnetic parts and appropriate rf filtering may be used to provide feedback to the incubator's temperature control system to provide suitable temperature control. In another embodiment of the disclosure, baffles may be provided to route heated air from the incubator 130 into and through the transfer table assembly 200.

The transfer table assembly of the present disclosure may be attached to the infant's incubator 130. One major function of the assembly may be to act as a buffer element to prevent non MR-compatible objects from entering into the magnet while the baby is inside the assembly.

As shown in FIG. 3, the safety barrier provided by the transfer table assembly 200 may be augmented with in-room barriers such as poles 350 in the floor spaced to prevent incubators or other devices from getting within a predetermined fringe magnetic field strength 360 (typically chosen to be 5 Gauss) at a selected distance 370 of the magnet. With such an approach the incubator 130 may be placed into a pre-dock position 340 where the transfer table assembly 220 may be attached and the neonate 110 may be moved and prepared for MR scanning. The ensemble of the transfer table assembly 200, neonate 110 and incubator 130 may then be moved towards MR scanner 102 along docking route 380. When the ensemble is in a docked location 330, the neonate 110 may be positioned at the isocenter 320 of the MR scanner 102.

Alternatively, the barrier may be augmented with a step design as shown in FIG. 4 in which the floor that accommodates the NICU incubator may be lower than a raised floor 410 surrounding the magnet. The step created by the two levels of the floor acts to align the incubator to the magnet as the transfer table assembly is inserted into the magnet. In an alternative embodiment of the disclosure, alignment mechanisms may be placed on the floor or at the base of the magnet to ensure proper alignment of the incubator during insertion.

The present disclosure has the advantage of working with incubators and isolettes that do not require modification to be made MR compatible. According to the present disclosure, the infant may, in one embodiment, still be tethered to the incubator by life support and monitoring methods, for example IV lines and EKG leads. Alternatively, the transfer table assembly 200 itself may be equipped with some or all of the aforementioned life support and monitoring methods.

The transfer table assembly may in one embodiment, as shown in FIG. 1b and FIG. 1c, be open like an isolette. In one embodiment, the open isolette may be configured with radiant heating. In another embodiment, the transfer table may be enclosed like an incubator with the addition of a cover. In one embodiment, the enclosed transfer table assembly may be configured to provide warm circulating air.

In one embodiment of the disclosure, the incubator may be adapted to dock to the MR scanner. This may be accomplished for instance by a mechanical latch which rigidly engages and may require a physical action to unlock, or it could be a simple "tongue and groove" arrangement in which the incubator can be brought close to the MR scanner with a selected alignment. In such an arrangement, it may be desirable to engage the wheel brakes on the incubator during docking to prevent the incubator from moving unexpectedly.

As mentioned, in one embodiment, the transfer table assembly 200 may be equipped to include all necessary life support and monitoring equipment. Such equipment includes, but is not limited to, EKG monitoring, IV tubes, oxygen monitors, ventilators, breathing gases, and bilirubin treatment. If needed, the transfer table assembly 200 can be powered by attachment to the incubator, an external supply or an on-board MR-compatible battery.

In one embodiment of the disclosure, the transfer table assembly 200 may comprise physical barriers to prevent extraneous objects being sucked into the infant when the infant is inside the magnet. In one embodiment, the barrier may comprise a full enclosure made of clear engineering plastic that is resistant to impact damage. This provides full visual access of the baby but provides a barrier to the entry of other objects into the magnet.

In one embodiment, a Faraday cage may be built into the transfer table assembly 200 to prevent RF interference from degrading the MR image. This would be particularly advantageous if the MR system is not placed in an RF screen room. Should a Faraday cage be incorporated into the transfer table assembly, an internal rf tight panel or door may need to be added between the incubator and the transfer table assembly. It may also be desirable to provide penetration filters for monitoring leads to minimize rf interference during MR imaging.

In an even further embodiment, the transfer table assembly may incorporate a scale for weighing the infants.

While the foregoing description includes many details and specificities, it is to be understood that these have been included for purposes of explanation only, and are not to be interpreted as limitations of the present disclosure. It will be apparent to those skilled in the art that other modifications to the embodiments described above can be made without departing from the spirit and scope of the disclosure. Accordingly, such modifications are considered within the scope of the disclosure as intended to be encompassed by the following claims and their legal equivalents.

What is claimed is:

1. A transfer table assembly suitable for use in association with an MR scanner and an incubator for neonatal infants, said transfer table assembly comprising:
   an MR-compatible transfer table base; and
   an attachment mechanism for releasably attaching said transfer table base to said incubator in a cantilevered fashion such that said transfer table base is cantilevered from said incubator substantially at the same vertical level of a scanning bore of an MR scanner;

said transfer table base being sized to be received within a scanning bore of an MR scanner, whereby as said incubator is moved towards and away from said scanning bore of said MR scanner, said cantilevered transfer table is correspondingly received within and removed from said scanning bore of said MR scanner.

2. The transfer table assembly as defined in claim 1, further comprising an MR-compatible transfer table cover adapted to be releasably attached to said transfer table base, wherein said transfer table base and transfer table cover are sized to be received within the scanning bore of the MR scanner.

3. The transfer table assembly as defined in claim 1, further comprising a supporting mechanism for providing structural support to said transfer table base when said transfer table base is attached to said incubator, wherein said supporting mechanism comprises a transfer table end plate extending substantially perpendicularly from said transfer table base, said end plate adapted to abut at least a portion of said incubator so as to provide structural support to said transfer table assembly.

4. The transfer table assembly as defined in claim 3, wherein said end plate further comprises one or more assembly insertion pins configured to align and releasably attach said transfer table assembly to the incubator.

5. The transfer table assembly of claim 1, wherein the transfer table assembly is equipped with life support and monitoring capabilities.

6. The transfer table assembly as defined in claim 1, wherein the transfer table is configured as an open isolette.

7. The transfer table assembly as defined in claim 1, wherein the transfer table assembly further comprises a scale for weighing the neonatal infant.

8. The transfer table assembly as defined in claim 1, further comprising a transfer table cart, wherein said transfer table base further comprises a securing mechanism configured to releasably attach said transfer table base to said transfer table cart in a cantilevered fashion.

9. A system for providing neonatal infants with magnetic resonance image testing, the system comprising:
   a) an incubator for neonatal infants;
   b) an MR scanner including a scanning bore; and
   c) a transfer table assembly comprising:
      an MR-compatible transfer table base sized to be received within said scanning bore; and
      an attachment mechanism for releasably attaching said transfer table base to said incubator in a cantilevered fashion such that said transfer table base is cantilevered from said incubator substantially at the same vertical level of said scanning bore;
   whereby as said incubator is moved towards and away from said scanning bore of said MR scanner, said cantilevered transfer table is correspondingly received within and removed from said scanning bore of said MR scanner.

10. The system of claim 9, wherein said incubator is at least partially enclosed and comprises at least one removable wall, and wherein said attachment mechanism is further configured to releasably attach said transfer table base to said incubator adjacently with a side of the incubator having said at least one removable wall.

11. The transfer table assembly as defined in claim 9, further comprising an MR-compatible transfer table cover adapted to be releasably attached to said transfer table base.

12. The system of claim 9 wherein said incubator includes a platform supporting a neonate bed, said platform adapted to be moved from said incubator onto said transfer table assembly.

13. The system of claim 9 wherein said transfer table assembly comprises a safety barrier adapted to prevent non-MRI compatible objects from entering into the MR scanner.

14. The system of claim 13 wherein said safety barriers comprise in-room barriers disposed on the floor about the system to prevent incubators and other devices from getting within a predetermined distance from the MR scanner.

15. The system of claim 14 where said safety barriers comprise at least one of a series of poles disposed on the floor about the MR scanner and a wall disposed on the floor about the MR scanner.

16. The system of claim 9, further comprising a transfer table cart adapted to support said transfer table assembly in a cantilevered fashion and to dock with said MR scanner.

17. The system as defined in claim 16, wherein said transfer table base further comprises a securing mechanism configured to releasably attach said transfer table base to said transfer table cart in a cantilevered fashion.

18. The system as defined in claim 17, wherein said cart is further configured to releasably engage said incubator.

19. A method of providing a neonatal infant with an MR imaging scan, the method comprising the steps of:
   a) providing an incubator with a neonatal baby laying on a bed therein, said incubator being at least partially enclosed and further comprising at least one removable wall and a moveable platform supporting said neonate bed;
   b) removing the removable wall;
   c) releasably installing a transfer table assembly onto said incubator adjacent to the side of the incubator in a cantilevered fashion where the removable wall was disposed, said transfer table assembly being adapted to support a neonatal infant thereon, said transfer table assembly further comprising an attachment mechanism for releasably attaching said transfer table base to said incubator in a cantilevered fashion such that said transfer table is cantilevered from said incubator substantially at the same vertical level of a scanning bore of an MR scanner, said transfer table assembly further being substantially MR compatible, and wherein the transfer table portion of the transfer table assembly is dimensionally constructed such that it may be inserted directly into said scanning bore of said MR scanner;
   d) transferring said platform supporting the bed and infant onto said transfer table assembly;
   e) preparing the infant for MR scanning;
   f) positioning said infant within said scanning bore of said MR scanner by engaging said transfer table assembly and incubator combination with the MR scanner, wherein said cantilevered transfer table assembly is inserted within said scanning bore of the MR scanner; and
   g) activating the MR scanner to obtain MR imaging of the infant.

20. The transfer table assembly as defined in claim 1, further comprising an MR-compatible, planar transfer table removably attached to a top surface of said transfer table base, said transfer table being configured to receive at least a portion of an incubator bed thereon.

21. The transfer table assembly as defined in claim 1, wherein said transfer table base is shaped as a lower half of a cylinder.

22. The transfer table assembly as defined in claim 2, wherein:
- said transfer table base is shaped as a lower half of a cylinder;
- said transfer table cover is shaped as an upper half of said cylinder; and
- said cylinder is sized to fit within said scanning bore of said MR scanner.

23. The transfer table assembly as defined in claim 2, wherein said transfer table base and said transfer table cover provide an extended internal volume that extends an internal volume of said incubator when said transfer table base is attached to said incubator in said cantilevered fashion.

24. The transfer table assembly as defined in claim 23, further comprising baffles adapted to route heated air from said incubator internal volume into said extended internal volume when said transfer table base is attached to said incubator in said cantilevered fashion.

25. The transfer table assembly as defined in claim 23, further comprising a means for heating air in said extended internal volume.

26. The system as defined in claim 11, wherein:
- said transfer table base is shaped as a lower half of a cylinder;
- said transfer table cover is shaped as an upper half of said cylinder; and
- said cylinder is sized to fit within said scanning bore of said MR scanner.

27. The system as defined in claim 11, wherein said transfer table base and said transfer table cover provide an extended internal volume that extends an internal volume of said incubator when said transfer table base is attached to said incubator in said cantilevered fashion.

* * * * *